United States Patent
Chen et al.

(10) Patent No.: US 8,658,605 B2
(45) Date of Patent: Feb. 25, 2014

(54) **BIOACTIVITY COMPOSITION OF *REEVESIA FORMOSANA***

(75) Inventors: Ih-Sheng Chen, Kaohsiung (TW); Hsun-Shuo Chang, Kaohsiung (TW)

(73) Assignee: Kaohsiung Medical University (TW)

( * ) Notice: Subject to any disclaimer, the term of this patent is extended or adjusted under 35 U.S.C. 154(b) by 24 days.

(21) Appl. No.: 13/252,328

(22) Filed: Oct. 4, 2011

(65) Prior Publication Data

US 2012/0258923 A1  Oct. 11, 2012

(30) Foreign Application Priority Data

Apr. 11, 2011  (TW) .............................. 100112521 A

(51) Int. Cl.
*A01N 43/04* (2006.01)
*A61K 31/56* (2006.01)
*A61K 31/585* (2006.01)

(52) U.S. Cl.
USPC .............................. 514/26; 514/169; 514/175

(58) Field of Classification Search
None
See application file for complete search history.

(56) References Cited

U.S. PATENT DOCUMENTS

2011/0311651 A1   12/2011   Djaballah et al.

FOREIGN PATENT DOCUMENTS

WO   2006120472 A2   11/2006
WO   2010068247 A1    6/2010

OTHER PUBLICATIONS

Ueda et al., Journal of Natural Products, 2003, 66(11), pp. 1427-1433.*
Pauli et al., Journal of Natural Products, 2010, 73(3), pp. 338-345.*
Jiang et al, Chem. Pharm. Bull., 56(7), 1005-1008, 2008.*
Abe et al., "Cardenolide Glycosides from the Roots of *Apocynum cannabinum*," Chem. Pharm. Bull. 42(10), pp. 2028-2031 (1994).
Kupchan et al., "Tumor Inhibitors. IV. Apocannoside and Cymarin, the Cytotoxic Principles of *Apocynum cannabinum* L." J. Med. Chem. 7 (6), pp. 803-804 (Nov. 1964).

* cited by examiner

Primary Examiner — Traviss C McIntosh, III

(74) *Attorney, Agent, or Firm* — Volpe and Koenig, P.C.

(57) ABSTRACT

A series cardenolide derivatives including structure of formula I from the root of *Reevesia formosana* have provided. In formula (1) and (2), where $R^3$, $R^5$, $R^{10}$ and $R^{16}$ are as defined in the specification. The derivatives compounds showed potent cytotoxicity against MCF-7, NCI-H460, and HepG2 cancer cell lines.

Formula (1)

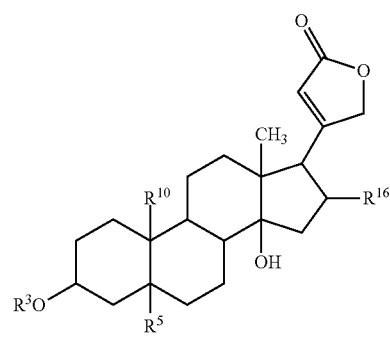

Formula (2)

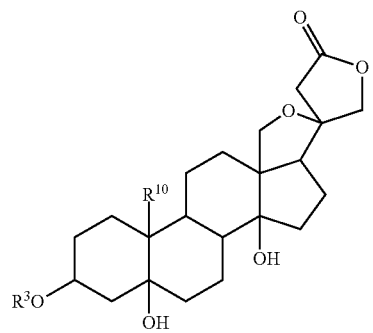

10 Claims, 1 Drawing Sheet

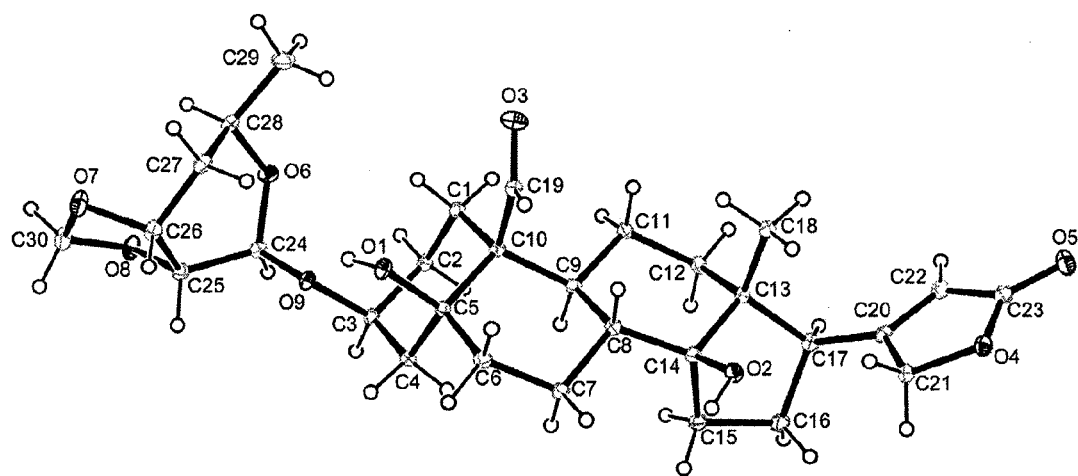

BIOACTIVITY COMPOSITION OF *REEVESIA FORMOSANA*

The application claims the benefit of Taiwan Patent Application No. 100112521, filed on Apr. 11, 2011, in the Intellectual Property Office of Republic of China, the disclosure of which is incorporated by reference as if fully set forth herein.

FIELD OF THE INVENTION

The present invention relates to a compound, in particular, to cardenolide derivatives from the root of *Reevesia formosana*, which showed the cytotoxic effects on cancer cells.

BACKGROUND OF THE INVENTION

*Reevesia formosana* Sprague is an endemic deciduous tree grows in southern Taiwan. There are about 25 species of Reevesia worldwide, with two species in central America, fourteen in mainland China, and one in Taiwan. The remainder are found mostly in Southeast Asia. In 2003, there were five known compounds which are β-sitosterol, daucosterol, betulinic acid, lupeol, (+)-catechin isolated from *R. longipetiolata*.

Nowadays, in research of natural, a separating strategy is usually put emphasis on active components. A collected natural is extracted by alcohol or aqueous alcohol, and the extractives are separated into fractions by different ionizing solvent partitions. Then, the each fraction is examined by every kind of biological activity test, and the fraction with active components is further examined by separating and extracting techniques to acquire physiological activities. Such examining model combined chemical components analyses and activity analyses is called bioassay-guided fractionation.

SUMMARY OF THE INVENTION

In accordance with a first aspect of the present invention, a pharmaceutical composition is provided and includes an effective amount of a pharmaceutical compound being represented by formula 1:

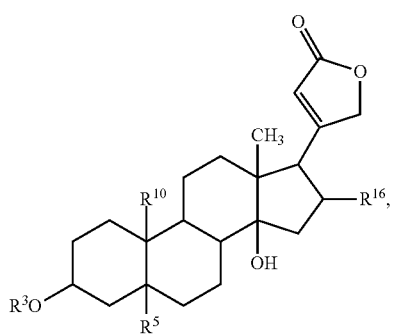

(1)

wherein the $R^3$ group is one of a hydrogen radical and a glycosyl group, the $R^5$ group is one of a hydrogen radical and a hydroxyl group, the $R^{10}$ group is one selected from a group consisting of a hydrogen radical, a hydroxyl group, a methyl radical, a formaldehyde group and a formic acid radical, and the $R^{16}$ group is one of a hydrogen radical and an acetic acid radical.

In accordance with a second aspect of the present invention, a pharmaceutical composition is provided and includes an effective amount of a pharmaceutical compound being represented by formula 2:

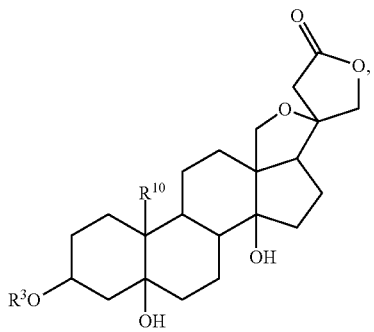

(2)

According to the above-mentioned aspects of the present invention, collected roots of *Reevesia formosana* were dried and cut into slices. Then, the slices were extracted by methanol in the room temperature. After eliminating the solvent, the extractive was partitioned into an EtOAc fraction and a water fraction by EtOAc and $H_2O$, wherein the EtOAc fraction was subjected to a silicon column, and a concentration gradient of n-hexane-EtOAc was applied on elution to acquire 1~12 fractions, and at last methanol was used to elute to form 13 fractions totally. The EtOAc fraction and the water fraction were conducted active examinations individually, and the result showed that the extractives have an cytotoxic effect on tumor cells of MCF-7, NCI-H460 and HepG2. Table. 1 shows that the fractions 9~13 have stronger cytotoxic effects on the tumor cells of MCF-7, NCI-H460 and HepG2.

TABLE 1

The survival rates of EtOAc fractions 9~13

| Cell line\fraction | | 9 | 10 | 11 | 12 | 13 |
|---|---|---|---|---|---|---|
| MCF-7 | 150 (μg/ml) | 9% | 4% | 8% | 8% | 8% |
| | 30 (μg/ml) | 38% | 5% | 6% | 6% | 5% |
| NCI-H460 | 150 (μg/ml) | 8% | 5% | 91% | 10% | 12% |
| | 30 (μg/ml) | 44% | 9% | 10% | 10% | 9% |
| HepG2 | 150 (μg/ml) | 4% | 2% | 2% | 2% | 3% |
| | 30 (μg/ml) | 2% | 1% | 1% | 1% | 1% |

According to the above-mentioned aspects of the present invention, materials of the column were selected from silicon, Sephadex LH-20, RP-$C_{18}$ etc. the following elution and purification were conducted via solvents of $CH_2Cl_2$, EtOAc, n-hexane, methanol, acetone, water and the mixtures thereof. See Table. 2, wherein the fraction 10 which was subjected to passage over a Sephadex LH-20 column, eluting with 100% methanol, to yield 13 fractions (fractions 10-1 to 10-13). The fraction 10-3 was separated over a RP-$C_{18}$ column, eluting with a solvent mixed by the methanol and the water with a ratio 3:2, and fractions 10-3-1 to 10-3-12 were obtained.

The fraction 10-3-6 was subjected to the silicon column, eluting with a mixing solvent of $CH_2Cl_2$-acetone (3:1), to furnish 7 fractions (fractions 10-3-6-1 to 10-3-6-7). The fraction to 10-3-10 was purified by the silicon column, eluting with a mixing solvent of $CH_2Cl_2$-acetone (3:1) to yield 5 fractions (fractions 10-3-10-1 to 10-3-10-5). The fraction 11 was applied to a Sephadex LH-20 column, eluting with 100% methanol, to afford 9 fractions (fractions 11-1 to 11-9). The fraction 11-2 was submitted to a RP-$C_{18}$ column, using a mixing solvent of methanol-water (1:1) for elution, to obtain 14 fractions (fractions 11-2-1 to 11-2-14). The fraction 11-2-8 was subjected to passage over a silicon column, eluting with a mixing solvent of CH$_2$Cl$_2$-acetone (3:1), to yield 9 fractions (fractions 11-2-8-1 to 11-2-8-9).

Besides, compound 1 (460 mg) was separated from the fraction 10-3-8, and a crystal mixture (10 mg) of compounds 8 and 9 was acquired from the fraction 10-3-5 by eluted with the solvent of n-hexane-EtOAc. After filtering out the crystal, the solution was subjected to the silicon column eluting with the mixing solvent of CH$_2$Cl$_2$-acetone (5:1), to obtain 7 fractions (fractions 10-3-5-1 to 10-3-5-7). The fraction 10-3-6-2 was purified by the RP-C$_{18}$ manufacturing TLC plate via the mixing solvent of acetone-water (1:1), and then compound 2 (2 mg) was acquired. The fractions 11-2-8-7 and 11-2-8-8 were purified by the manufacturing TLC plate via the mixing solvent of n-hexane-CH$_2$Cl$_2$-acetone (1:1:2), and then compounds 3 (9 mg), 4 (14 mg), 5 (2.8 mg) and 6 (11 mg) were acquired. The fraction 10-3-10-3 and fraction 10-3-10-4 contained compounds 7 (63 mg) and 6 (11 mg), respectively. The fraction 10-3-5-2 contained a mixture (1.7 mg) of compounds 12 and 13, and the fraction 10-3-5-5 contained a mixture (7 mg) of compounds 10 and 11.

TABLE 2

| | | |
|---|---|---|
| A | EtOAc solvable fraction was subjected to the silicone column. | |
| | solvent  n-hexane | fraction 1 |
| | n-hexane/EtOAc (90:10~85:15~80:20~70:30~50:50) | fractions 2~9 |
| | EtOAc | fractions 10~12 |
| | methanol | fraction 13 |
| B | fraction 10 was subjected to passage over a Sephadex LH-20 column. | |
| | solvent  methanol | fractions 10-1 to 10-13 |
| C | fraction 10-3 was separated over a RP-C$_{18}$ column. | |
| | solvent  methanol:water (3:2) | fractions 10-3-1~10-3-12 |
| D | Filter out the crystal mixture of compound 8 and 9, and the solution was subjected to the silicone column. | |
| | solvent  CH$_2$Cl$_2$-acetone (5:1) | fractions 10-3-5-1~10-3-5-7 |
| E | fraction 10-3-6 was subjected to the silicone column. | |
| | solvent  CH$_2$Cl$_2$-acetone (3:1) | fractions 10-3-6-1~10-3-6-7 |
| F | fraction 10-3-6-2 was purified by RP-18 manufacturing TLC plate. | |
| | solvent  acetone-water (1:1) | |
| G | fraction 10-3-10 was purified by the silicone column. | |
| | solvent  CH$_2$Cl$_2$-acetone (3:1) | fractions 10-3-10-1~10-3-10-5 |
| H | fraction 11 was applied to a Sephadex LH-20 column. | |
| | solvent  methanol | fractions 11-1 to 11-9 |
| I | fraction 11-2 was submitted to a RP-C$_{18}$ column. | |
| | solvent  methanol:water (1:1) | fractions 11-2-1 to 11-2-14 |
| J | fraction 11-2-8 was subjected to passage over a silicone column. | |
| | solvent  CH$_2$Cl$_2$-acetone (3:1) | fractions 11-2-8-1 to 11-2-8-9 |

The separated and purified compounds were individually examined by a Yanaco micromelting apparatus, by related equipments to test NMR of UV, KBr, $^1$H and $^{13}$C and by single-crystal x-ray crystallography to confirm the structures of compounds. As shown in FIG. 1 is a monocrystal x-ray diffractogram of compound 1.

The NMR spectra of $^1$H and $^{13}$C of the compounds 10 and 11 were similar to spectra of the compounds 8 and 9, except that the aldehyde group [$\delta_H$ 10.05 (1H, s, H-19); $\delta_C$ 207.9 (C-19)] of 8 and 9 was replaced by a carboxylic acid group [$\delta_C$ 176.0 (C-19)] in 10 and 11. The compounds 12 and 13 were also duplicated the pattern of $^1$H and $^{13}$C NMR signals concerning the 18,20-epoxide structures of 8 and 9.

Cardenolides are found in Apocynaceae, Asclepiadaceae, Asteraceae, Brassicaceae, Euphorbiaceae, Liliaceae, Moraceae, Ranunculaceae, and Scrophulariaceae. Via the bioassay-guided-fractionation, the collected root of *Reevesia formosana* was demonstrated that its EtOAc and water fractions have cytotoxic effects on human breast adenocarcinoma (MCF-7) non-small-cell lung cancer (NCI-H460) and liver hepatocellular cells (HepG2). The purified cardenolide derivatives can be divided into the compounds as presented in formula 1 and 2 according to the physical and chemical properties (Tables. 4~9), wherein the compounds 8 and 9 were mixed with ratio 6:5, and the compounds 10 and 11, and the compounds 12 and 13 were both mixed with ratio 3:2. As shown in Table. 3, the cardenolide derivatives have cytotoxic effects on tumor cells of MCF-7, NCI-H460 and HepG2.

TABLE 3

IC$_{50}$ of 13 cardenolide derivatives

| | IC$_{50}$ (nM) | | |
|---|---|---|---|
| Compounds | MCF-7 | NCI-H460 | HepG2 |
| reevesioside A (1) | 63.2 ± 2.1 | 19.3 ± 0.5 | 367.6 ± 29.9 |
| reevesioside B (2) | 3524.3 ± 72.0 | 431.1 ± 45.1 | 4755.3 ± 202.5 |
| reevesioside C (3) | 2036.2 ± 172.8 | 207.9 ± 15.6 | 3738.4 ± 261.1 |
| reevesioside D (4) | 36427.0 ± 2577.5 | 3904.4 ± 316.2 | >500000 |
| reevesioside E (5) | 11764.2 ± 2239.4 | 1769.6 ± 35.4 | 40491.5 ± 6425.4 |
| reevesioside F (6) | 72.0 ± 8.1 | 20.3 ± 0.4 | 836.2 ± 33.2 |
| epi-reevesioside F (7) | 34.1 ± 5.5 | 10.4 ± 0.5 | 995.5 ± 92.6 |
| mixture of reevesioside G (8) and epi-reevesioside G (9) | 2070.8 ± 52.6 | 485.6 ± 29.3 | 8903.9 ± 790.7 |
| mixture of reevesioside H (10) and epi-reevesioside H (11) | 36194.2 ± 4128.6 | 3665.3 ± 182.5 | >500000 |
| mixture of reevesioside I (12) and epi-reevesioside I (13) | 9352.9 ± 962.9 | 1090.8 ± 207.0 | 22739.3 ± 3489.7 |
| tylophorine* | 236.0 ± 11.0 | 233.0 ± 24.0 | 215 ± 14.0 |

*Positive control

In the formula 1 of compound, the R$^3$ group is one of a hydrogen radical and a glycosyl group, the R$^5$ group is one of a hydrogen radical and a hydroxyl group, the R$^{10}$ group is one selected from a group consisting of a hydrogen radical, a hydroxyl group, a methyl radical, a formaldehyde group and a formic acid radical, and the R$^{16}$ group is one of a hydrogen radical and an acetic acid radical.

The formula 2 of compound, the R$^3$ group is one of a hydrogen radical and a glycosyl group, the R$^{10}$ group is one selected from a group consisting of a hydrogen radical, a hydroxyl group, a methyl radical, a formaldehyde group, and a formic acid radical.

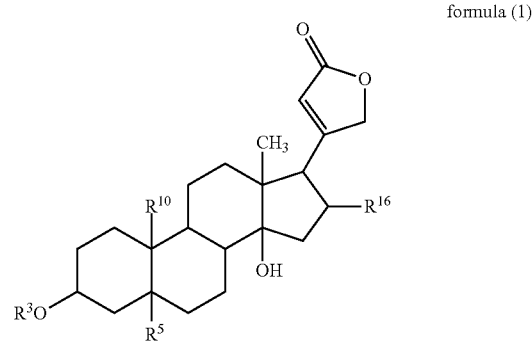

formula (1)

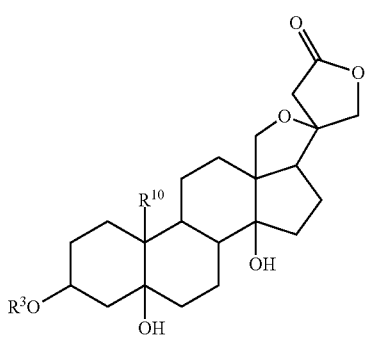

formula (2)

$R^3$ group is a special glycosyl group which are reevesiosyl group (a), 4,6-dideoxy-2-O-methyl-β-D-allosyl group (b), 6-deoxy-2-O-methyl-β-D-glycosyl group (c), 6-deoxy-2-O-methyl-β-D-allosyl group (d).

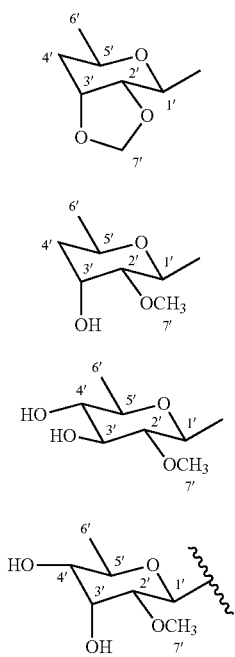

The root of *Reevesia formosana* contains 13 cardenolide derivatives. The compounds, reevesiodides A-I, were assigned 1~6,8,10 and 12, and epi-reevesiosides F-I were assigned 7, 9, 11 and 13. Structures of the reevesiosides A-F and the epi-reevesioside F belong to formula 1, and structures of the reevesiosides G-I and the epi-reevesiosides G-I belong to formula 2.

| Formula 1 | substituted group | | | |
|---|---|---|---|---|
| | $R^3$ | $R^5$ | $R^{10}$ | $R^{16}$ |
| reevesioside A (1) | a | OH | CHO | H |
| reevesioside B (2) | a | OH | CHO | OAc |
| reevesioside C (3) | b | OH | CHO | H |
| reevesioside D (4) | b | OH | COOH | H |
| reevesioside E (5) | b | OH | OH | H |
| reevesioside F (6) | c | H | $CH_3$ | H |
| epi-reevesioside F (7) | d | H | $CH_3$ | H |

| Formula 2 | substituted group | |
|---|---|---|
| | $R^3$ | $R^{10}$ |
| reevesioside G (8) | a (20S) | CHO |
| epi-reevesioside G (9) | a (20R) | CHO |
| reevesioside H (10) | a (20S) | COOH |
| epi-reevesioside H (11) | a (20R) | COOH |
| reevesioside I (12) | a (20S) | OH |
| epi-reevesioside I (13) | a (20R) | OH |

According to the above mention that via bioassay-guided-fractionation, the EtOAc soluable fraction (Table. 1 and Table. 3) shows that the above 13 ardenolide derivatives have cytotoxic effects on MCF-7, NCI-H460 and HepG2.

The term excipients or "pharmaceutically acceptable carrier or excipients" and "bio-available carriers or excipients" mentioned above include any appropriate compounds known to be used for preparing the dosage form, such as the solvent, the dispersing agent, the coating, the anti-bacterial or anti-fungal agent and the preserving agent or the delayed absorbent. Usually, such kind of carrier or excipient does not have the therapeutic activity itself. Each formulation prepared by combining the derivatives disclosed in the present invention and the pharmaceutically acceptable carriers or excipients will not cause the undesired effect, allergy or other inappropriate effects while being administered to an animal or human. Accordingly, the derivatives disclosed in the present invention in combination with the pharmaceutically acceptable carrier or excipients are adaptable in the clinical usage and in the human. A therapeutic effect can be achieved by using the dosage form in the present invention by the local or sublingual administration via the venous, oral, and inhalation routes or via the nasal, rectal and vaginal routes. About 0.1 mg to 1000 mg per day of the active ingredient is administered for the patients of various diseases.

The carrier is varied with each formulation, and the sterile injection composition can be dissolved or suspended in the non-toxic intravenous injection diluents or solvent such as 1,3-butanediol. Among these carriers, the acceptable carrier may be mannitol or water. Besides, the fixing oil or the synthetic glycerol ester or di-glycerol ester is the commonly used solvent. The fatty acid such as the oleic acid, the olive oil or the castor oil and the glycerol ester derivatives thereof, especially the oxy-acetylated type, may serve as the oil for preparing the injection and as the naturally pharmaceutical acceptable oil. Such oil solution or suspension may include the long chain alcohol diluents or the dispersing agent, the carboxylate methyl cellulose (CMC) or the analogous dispersing agents, such as methyl cellulose, ethyl cellulose and hydroxylethyl methyl cellulose (HEMC). Other carriers are common surfactant such as Tween and Spans or other analogous emulsion, or the pharmaceutically acceptable solid, liquid or other bio-available enhancing agent used for developing the formulation that is used in the pharmaceutical industry.

The composition for oral administration adopts any oral acceptable formulation, which includes capsule, tablet, pill, emulsion, aqueous suspension, dispersing agent and solvent. The carrier is generally used in the oral formulation. Taking the tablet as an example, the carrier may be the lactose, the corn starch and the lubricant, and the magnesium stearate is the basic additive. The diluents used in the capsule include the lactose and the dried corn starch. For preparing the aqueous suspension or the emulsion formulation, the active ingredient is suspended or dissolved in an oil interface in combination with the emulsion or the suspending agent, and the appropriate amount of the sweetening agent, the flavors or the pigment is added as needed.

The nasal aerosol or inhalation composition may be prepared according to the well-known preparation techniques. For example, the bioavailability can be increased by dissolving the composition in the phosphate buffer saline and adding the benzyl alcohol or other appropriate preservative, or the absorption enhancing agent. The compound of the present invention may be formulated as suppositories for rectal or virginal administration.

The compound of the present invention can also be administered intravenously, as well as subcutaneously, parentally, muscular, or by the intra-articular, intracranial, intra-articular fluid and intra-spinal injections, the aortic injection, the sterna injection, the intra-lesion injection or other appropriate administrations. For different patients, an administering dosage is between 0.1 mg to 0.2 mg of active components per day.

The above objectives and advantages of the present invention will become more readily apparent to those ordinarily skilled in the art after reviewing the following detailed descriptions and accompanying drawings, in which:

BRIEF DESCRIPTION OF THE DRAWINGS

FIG. 1 a monocrystal x-ray diffractogram of the compound 1.

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Biological Experiments

1. Materials

MCF-7 (human breast adenocarcinoma), NCI-H460 (non-small-cell lung cancer) and HepG2 (liver hepatocellular cells) were incubated in a modified Dulbecco's Eagle's medium with 10% FBS and nonessential amino acid (liver Technologies, Inc) in an incubator with 37° C., 5% $CO_2$/Air. Human cancer cell lines were planted in 96-well plates, and each well which contained the 100 μl medium were planted one of MCF-7 and NCI-H460 with a cell amount of 6500, 2500 and 7500. After overnight incubation, each cell line was administered at least 8 testing compounds with different concentrations individually, and subsequently the cell lines were incubated in the incubator for 72 hours. According to a method of MTS reduction assay, 5-(3-carboxymethoxyphenyl)-2-(4,5-dimethylthiazoyl)-3-(4-sulfophenyl)tetrazolium salt (MTS) was applied on estimating alive cell numbers, and 0.1% DMSO (Promega, Madison, Wis., USA) was a control group because DMSO controlled a result of percentage, the result could be a dose-response curve of $IC_{50}$ value. When the $IC_{50}$ value≤4 μg/ml, it was considered to have an obvious cytotoxic effect. The $IC_{50}$ value was an average of three times repeats. The 10000/well HepG2 cells were planted on a 96-well plate and were gone through the same experiences.

2. Extraction and Fractionation 6.5 kg dried roots of *Reevesia formosana* were cut into slices. Then, the slices were extracted by 30 L methanol for three times in the room temperature. After eliminating the solvent, the 150 g methanolic extractive was partitioned into an EtOAc fraction and a water fraction by EtOAc and $H_2O$, and 45 g EtOAc fraction and 100 g water fraction were acquired. These two fractions were had active examination, and results showed that the methanolic extractive had been shown cytotoxicity against MCF-7, NCI-H460 and HepG2 cancer cell lines.

The 45 g EtOAc fraction was subjected to a silicon column (70-230 sieve, 1.5 kg), and a concentration gradient of n-hexane-EtOAc was applied on elution to acquire 1~12 fractions, and at last methanol was used to elute to form 13 fractions totally. The fractions 9~13 had been shown cytotoxicity against MCF-7, NCI-H460 and HepG2 cancer cell lines.

The fraction 10 which was subjected to passage over a Sephadex LH-20 column, eluting with 100% methanol, to yield 13 fractions (fractions 10-1 to 10-13). The fraction 10-3 (0.87 g) was separated over a RP-$C_{18}$ column (20-40 μm silicon), eluting with a mixing solvent of the methanol-water (3:2), and fractions 10-3-1 to 10-3-12 were obtained. Compound 1 (460 mg) was separated from the fraction 10-3-8, and a crystal mixture (10 mg) of compounds 8 and 9 was acquired from the fraction 10-3-5 by eluted with the solvent of n-hexane-EtOAc. After filtering out the crystal, the solution was subjected to the silicon column, eluting with the mixing solvent of $CH_2Cl_2$-acetone (5:1), to obtain 7 fractions (fractions 10-3-5-1 to 10-3-5-7).

The fraction 10-3-5-2 contained a mixture (1.7 mg) of compounds 12 and 13, and the fraction 10-3-5-5 contained a mixture (7 mg) of compounds 10 and 11. The fraction 10-3-6 (14.3 g) was subjected to the silicon column (15-35 μm silicon), eluting with a mixing solvent of $CH_2Cl_2$-acetone (3:1), to furnish 7 fractions (fractions 10-3-6-1 to 10-3-6-7). The fraction 10-3-6-2 was purified by the RP-$C_{18}$ manufacturing TLC plate via the mixing solvent of acetone-water (1:1), and then compound 2 (2 mg) was acquired. The fraction 10-3-10 was purified by the silicon column, eluting with a mixing solvent of $CH_2Cl_2$-acetone (3:1), to yield 5 fractions (fractions 10-3-10-1 to 10-3-10-5). The fraction 10-3-10-3 and fraction 10-3-10-4 contained compounds 7 (63 mg) and 6 (11 mg), respectively. The fraction 11 (9 g) was applied to a Sephadex LH-20 column and was eluted by 100% methanol, to afford 9 fractions (fractions 11-1 to 11-9). The fraction 11-2 (0.74 g) was subjected to a RP-$C_{18}$ column (20-40 μm silicon) using a mixing solvent of methanol-water (1:1) for elution, to obtain 14 fractions (fractions 11-2-1 to 11-2-14). The fraction 11-2-8 (149 mg) was subjected to passage over a silicon column (15-35 μm silicon) eluting with a mixing solvent of $CH_2Cl_2$-acetone (3:1), to yield 9 fractions (fractions 11-2-8-1 to 11-2-8-9).

Besides, The fractions 11-2-8-7 and 11-2-8-8 were purified by the manufacturing TLC plate via the mixing solvent of n-hexane-$CH_2Cl_2$-acetone (1:1:2), and then compounds 3 (9 mg), 4 (14 mg), 5 (2.8 mg) and 6 (11 mg) were acquired.

3. Embodiment

Preparation of Composition of Injection

According to quantities of the components, the components were measured and taken to be dissolved in a liquid for preparation injections.
Reevesiosides A 0.135 mg/vial (1.1 mL)
Liquid for infection qs

TABLE 4

Data of physical properties of the compounds 1~13

Reevesioside A (1): colorless prisms
mp 231-232° C.;
$[\alpha]^{26}{}_D$ −28.7 (c 0.80, MeOH);
IR (KBr) $v_{max}$ 3518 (OH), 1780, 1744, 1621 (butenolactone ring), 1715 (CHO) cm$^{-1}$;
ESIMS m/z 569 [M + Na]$^+$;
HRESIMS m/z 569.2729 (calcd for $C_{30}H_{42}O_9Na$, 569.2726).
Reevesioside B (2): colorless syrup
$[\alpha]^{26}{}_D$ −18.7 (c 0.07, MeOH);
IR (neat) $v_{max}$ 3511 (OH), 1775, 1741, 1628 (butenolactone ring) cm$^{-1}$;
ESIMS m/z 627 [M + Na]$^+$;
HRESIMS m/z 627.2777 (calcd for $C_{32}H_{44}O_{11}Na$, 627.2781).
Reevesioside C (3): colorless needles
mp 140-142° C.;
$[\alpha]^{26}{}_D$ −20.7 (c 0.08, MeOH);
IR (KBr) $v_{max}$ 3498 (OH), 1779, 1744, 1621 (butenolactone ring), 1712 (CHO) cm$^{-1}$;
ESIMS m/z 571 [M + Na]$^+$;
HRESIMS m/z 571.2881 (calcd for $C_{30}H_{44}O_9Na$, 571.2883).
Reevesioside D (4): colorless needles
mp 160-162° C.;
$[\alpha]^{26}{}_D$ −14.1 (c 0.12, MeOH);
IR (KBr) $v_{max}$ 3499 (OH), 1780, 1746, 1621 (butenolactone ring), 2500-3300, 1730 (COOH) cm$^{-1}$;
ESIMS m/z 587 [M + Na]$^+$;
HRESIMS m/z 587.2836 (calcd for $C_{30}H_{44}O_{10}Na$, 587.2832).
Reevesioside E (5): colorless needles
mp 228-229° C.;
$[\alpha]^{26}{}_D$ −10.3 (c 0.04, MeOH);
IR (KBr) $v_{max}$ 3479 (OH), 1779, 1745, 1620 (butenolactone ring) cm$^{-1}$;
ESIMS m/z 559 [M + Na]$^+$;
HRESIMS m/z 559.2886 (calcd for $C_{29}H_{44}O_9Na$, 559.2883).
Reevesioside F (6): colorless needles
mp 241-242° C.;
$[\alpha]^{26}{}_D$ −17.6 (c 0.08, MeOH);
IR (KBr) $v_{max}$ 3442 (OH), 1779, 1742, 1622 (butenolactone ring) cm$^{-1}$;
ESIMS m/z 557 [M + Na]$^+$;
HRESIMS m/z 557.3088 (calcd for $C_{30}H_{46}O_8Na$, 557.3090).
epi-Reevesioside F (7): colorless needles
mp 216-217° C.;
$[\alpha]^{26}{}_D$ −16.9 (c 1.20; MeOH);
IR (KBr) $v_{max}$ 3458 (OH), 1780, 1741, 1621 (butenolactone ring) cm$^{-1}$;
ESIMS m/z 557 [M + Na]$^+$;
HRESIMS m/z 557.3094 (calcd for $C_{30}H_{46}O_8Na$, 557.3090).
Mixed Reevesioside G (8) and epi-Reevesioside G (9): colorless syrup
$[\alpha]^{26}{}_D$ −46.7 (c 0.12, MeOH);
IR (neat) $v_{max}$ 3524 (OH), 1780 (lactone ring), 1712 (CHO) cm$^{-1}$;
ESIMS m/z 585 [M + Na]$^+$;
HRESIMS m/z 585.2672 (calcd for $C_{30}H_{42}O_{10}Na$, 585.2676).
Mixed Reevesioside H (10) and epi-Reevesioside H (11): colorless syrup
$[\alpha]^{26}{}_D$ −13.3 (c 0.20, MeOH);
IR (neat) $v_{max}$ 3521 (OH), 1780 (lactone ring), 2500-3300, 1727, (COOH) cm$^{-1}$;
ESIMS m/z 601 [M + Na]$^+$;
HRESIMS m/z 601.2621 (calcd for $C_{30}H_{42}O_{11}Na$, 601.2625).
Mixed Reevesioside I (12) and epi-Reevesioside I (13): colorless syrup
$[\alpha]^{26}{}_D$ −27.1 (c 0.10, MeOH);
IR (neat) $v_{max}$ 3520 (OH), 1781 (lactone ring) cm$^{-1}$;
ESIMS m/z 573 [M + Na]$^+$;
HRESIMS m/z 573.2679 (calcd for $C_{29}H_{42}O_{10}Na$, 573.2676).

TABLE 5

$^1$H NMR data of compounds 1~5$^a$

| position | 1 | 2 | 3 | 4 | 5 |
|---|---|---|---|---|---|
| 1a/b | 2.22, m/ 1.69, m | 2.30, m/ 1.71, m | 2.23, m/ 1.72, m | 2.36, m/ 1.46, m | 1.89, m/ 1.49, m |
| 2a/b | 1.91, m/ 1.51, m | 1.98, m/ 1.52, m | 1.93, m/ 1.54, m | 1.94, m/ 1.59, m | 1.81, m/ 1.74, m |
| 3 | 4.18, br s | 4.21, br t (2.7) | 422, br s | 4.25, br s | 4.17, br t, (2.7) |
| 4a/b | 1.97, m/ 1.68, m | 1.96, m/ 1.72, m | 1.94, m/ 1.72, m | 2.08, m/ 1.79, m | 1.88, m/ 1.45, m |
| 6a/b | 2.06, m/ 1.68, m | 2.04, m/ 1.71, m | 2.07, m/ 1.72, m | 1.77, m/ 1.69, m | 1.86, m/ 1.45, m |
| 7a/b | 2.08, m/ 1.23, m | 2.08, m/ 1.18, m | 2.09, m/ 1.25, m | 2.04, m/ 1.15, m | 1.87, m/ 1.06, m |
| 8 | 1.91, m | 1.97, m | 1.92, m | 1.98, m | 1.81, m |
| 9 | 1.51, m | 1.43, m | 1.52, m | 1.52, m | 1.43, m |
| 11a/b | 1.50, m/ 1.30, m | 1.51, m/ 1.38, m | 1.54, m/ 1.31, m | 2.26, m/ 1.86, m | 1.58, m |
| 12a/b | 1.51, m/ 1.32, m | 1.57, m/ 1.22, m | 1.52, m/ 1.33, m | 1.52, m/ 1.35, m | 1.56, m/ 1.43, m |
| 15a/b | 2.00, m/ 1.66, m | 2.63, dd (15.9, 9.6)/ 1.76, dd (15.9, 2.7) | 2.01, m/ 1.68, m | 1.93, m/ 1.72, m | 2.00, m/ 1.68, m |
| 16a/b | 2.14, m/ 1.86, m | 5.45, dd (9.6, 8.6, 2.7) | 2.17, m/ 1.85, m | 2.12, m/ 1.88, m | 2.15, m/ 1.86, m |
| 17 | 2.75, dd (9.8, 5.4) | 3.18, d (8.6) | 2.75, dd (9.6, 5.2) | 2.76, dd (9.2, 4.8) | 2.77, dd (9.6, 5.4) |
| 18 | 0.85, s | 0.94, s | 0.86, s | 0.97, s | 0.92, s |
| 19 | 10.0, s | 10.0, d (0.8) | 10.05, s | | |
| 21a/b | 4.95, dd (18.0, 1.6)/ 4.79, dd (18.0, 1.6) | 4.95, dd (18.3, 1.8)/ 4.85, dd (18.3, 1.8) | 4.95, dd (18.2, 1.6)/ 4.79, dd (18.2, 1.6) | 4.98, dd (18.2, 1.4)/ 4.81, dd (18.2, 1.4) | 4.96, dd (18.0, 1.5)/ 4.81, dd (18.0, 1.5) |
| 22 | 5.86, s | 6.00, s | 5.88, s | 5.88, s | 5.88, s |
| 25 | | 1.98, s | | | |
| 1' | 4.46, d (6.8) | 4.47, d (6.9) | 4.74, d (7.9) | 4.73, d (7.9) | 4.74, d (8.0) |
| 2' | 3.79, dd (6.8, 5.4) | 3.82, dd (6.9, 5.4) | 3.01, dd (7.9, 3.0) | 3.03, dd (7.9, 3.0) | 3.02, dd (8.0, 3.3) |
| 3' | 4.13, ddd (5.4, 4.0, 1.8) | 4.14, ddd (5.4, 4.2, 1.8) | 4.27, m | 4.30, m | 4.28, m |
| 4'a/b | 2.12, m/ 1.76, m | 2.15, m/ 1.72, m | 1.92, m/ 1.49, m | 1.95, m/ 1.49, m | 1.93, m/1.47, m |
| 5' | 3.79, m | 3.83, m | 3.98, m | 3.99, m | 3.99, m |
| 6' | 1.22, d (6.4) | 1.25, d (6.0) | 1.19, d (6.0) | 1.19, d (6.0) | 1.20, d (6.6) |
| 7'a/b | 5.21, s/ 4.88, s | 5.23, s/ 4.90, s | 3.43, s | 3.44, s | 3.47, s |
| OH-5$^b$ | 4.25, s | 4.30, s | 4.49, s | | 4.39, s |

$^a$ $^1$H NMR data (δ) were measured in CDCl$_3$ at 400 MHz for 1, 3, and 4, at 600 MHz for 2 and 5.
$^b$ D$_2$O exchangeable

TABLE 6

$^{13}$C NMR data of compound 1~7$^a$

| position | 1 | 2 | 3 | 4 | 5 | 6 | 7 |
|---|---|---|---|---|---|---|---|
| 1 | 17.8 | 18.0 | 17.9 | 21.3 | 28.6 | 30.3 | 30.2 |
| 2 | 25.3 | 25.3 | 25.4 | 25.7 | 26.1 | 26.6 | 26.6 |
| 3 | 73.0 | 73.1 | 72.0 | 72.2 | 72.4 | 73.2 | 73.1 |
| 4 | 34.5 | 34.4 | 34.0 | 33.2 | 34.3 | 29.5 | 29.5 |
| 5 | 73.4 | 73.2 | 73.1 | 74.6 | 73.71$^b$ | 36.4 | 36.3 |
| 6 | 36.3 | 36.3 | 36.5 | 36.5 | 34.5 | 26.6 | 26.6 |
| 7 | 24.1 | 23.7 | 24.2 | 23.9 | 23.5 | 21.4 | 21.3 |
| 8 | 41.6 | 41.5 | 41.7 | 40.7 | 40.5 | 41.8 | 41.7 |
| 9 | 39.3 | 39.1 | 39.3 | 39.4 | 39.8 | 35.8 | 35.7 |
| 10 | 54.6 | 54.3 | 54.6 | 53.3 | 73.74$^b$ | 35.2 | 35.1 |
| 11 | 21.9 | 21.4 | 21.9 | 21.8 | 21.0 | 21.1 | 21.1 |
| 12 | 39.7 | 39.0 | 39.7 | 40.0 | 40.0 | 40.0 | 39.9 |
| 13 | 49.4 | 49.8 | 49.4 | 49.8 | 49.5 | 49.6 | 49.6 |

TABLE 6-continued

¹³C NMR data of compound 1~7[a]

| position | 1 | 2 | 3 | 4 | 5 | 6 | 7 |
|---|---|---|---|---|---|---|---|
| 14 | 85.1 | 84.0 | 85.2 | 85.3 | 85.2 | 85.6 | 85.5 |
| 15 | 31.9 | 40.1 | 32.0 | 32.3 | 32.6 | 33.1 | 33.0 |
| 16 | 26.8 | 73.7 | 26.8 | 26.8 | 26.9 | 26.9 | 26.8 |
| 17 | 50.4 | 55.6 | 50.4 | 50.4 | 50.6 | 50.9 | 50.8 |
| 18 | 15.5 | 15.8 | 15.6 | 15.6 | 15.7 | 15.7 | 15.7 |
| 19 | 208.2 | 208.1 | 208.3 | 176.6 |  | 23.8 | 23.8 |
| 20 | 174.5[b] | 167.2 | 174.4[b] | 174.7[b] | 174.44[c] | 174.54[b] | 174.8[b] |
| 21 | 73.3 | 75.5 | 73.4 | 73.6 | 73.4 | 73.4 | 73.5 |
| 22 | 117.7 | 121.6 | 117.9 | 117.6 | 117.7 | 117.7 | 117.5 |
| 23 | 174.3[b] | 173.9 | 174.1[b] | 174.6[b] | 174.38[c] | 174.53[b] | 174.7[b] |
| 24 |  | 170.5 |  |  |  |  |  |
| 25 |  | 21.1 |  |  |  |  |  |
| 1' | 99.1 | 99.3 | 96.5 | 96.5 | 96.5 | 100.6 | 97.8 |
| 2' | 73.7 | 73.8 | 80.7 | 80.5 | 80.7 | 83.3 | 80.2 |
| 3' | 74.5 | 74.6 | 64.6 | 64.3 | 64.6 | 76.3 | 69.9 |
| 4' | 34.3 | 34.3 | 38.1 | 38.1 | 38.1 | 75.2 | 72.8 |
| 5' | 67.0 | 67.1 | 66.5 | 66.7 | 66.5 | 71.4 | 69.5 |
| 6' | 20.9 | 20.9 | 20.6 | 20.6 | 20.6 | 17.6 | 17.7 |
| 7' | 95.4 | 95.4 | 57.6 | 57.3 | 57.6 | 60.8 | 59.4 |

[a]¹³C NMR data (δ) were measured in CDCl₃ at 100 MHz for 1, 3, 4, 6, and 7, at 150 MHz for 2 and 5.
[b,c]Interchangeable within the same column.

TABLE 7

¹H NMR data of compounds 6~9[a]

| Position | 6 | 7 | 8 | 9 |
|---|---|---|---|---|
| 1a/b | 1.50, m | 1.48, m | 2.13, m/ 1.67, m | 2.13, m/ 1.67, m |
| 2a/b | 1.69, m/ 1.52, m | 1.66, m/ 1.48, m | 1.92, m/ 1.48, m | 1.92, m/ 1.48, m |
| 3 | 4.08, br s | 4.03, br s | 4.17, br s | 4.17, br s |
| 4a/b | 1.70, m/ 1.23, m | 1.69, m/ 1.23, m | 1.95, m/ 1.67, m | 1.95, m/ 1.67, m |
| 5 | 1.72, m | 1.69, m |  |  |
| 6a/b | 1.88, m/ 1.28, m | 1.84, m/ 1.26, m | 2.18, m/ 1.67, m | 2.18, m/ 1.67, m |
| 7a/b | 1.69, m/ 1.26, m | 1.67, m/ 1.18, m | 2.19, m/ 1.26, m | 2.19, m/ 1.26, m |
| 8 | 1.56, m | 1.53, m | 1.90, m | 1.90, m |
| 9 | 1.61, m | 1.59, m | 1.38, m | 1.38, m |
| 11a/b | 1.44, m/ 1.26, m | 1.38, m/ 1.18, m | 1.61, m/ 0.83, m | 1.61, m/ 0.83, m |
| 12a/b | 1.52, m/ 1.39, m | 1.51, m/ 1.40, m | 1.67, m/ 1.42, m | 1.67, m/ 1.42, m |
| 15a/b | 2.13, m/ 1.69, m | 2.11, m/ 1.68, m | 1.79, m/ 1.67, m | 1.79, m/ 1.67, m |
| 16a/b | 2.16, m/ 1.88, m | 2.14, m/ 1.84, m | 1.93, m/ 1.68, m | 1.92, m/ 1.61, m |
| 17 | 2.78, dd (8.8, 5.2) | 2.76, dd (9.2, 4.8) | 2.10, m | 2.30, dd (9.2, 8.0) |
| 18a/b | 0.87, s | 0.85, s | 4.13, d (10)/ 3.40, d (10) | 4.15, d (10)/ 3.36, d (10) |
| 19 | 0.93, s | 0.91, s | 10.05, s | 10.05, s |
| 21a/b | 4.99, dd (18.1, 1.7)/ 4.81, dd (18.1, 1.7) | 4.98, dd (18.0, 1.6)/ 4.79, dd (18.0, 1.6) | 4.31, dd (10, 0.8)/ 3.97, d (10) | 4.34, s |
| 22a/b | 5.88, s | 5.85, s | 2.64, d (17.4)/ 2.57, dd (17.4, 0.8) | 2.71, d (17.4)/ 2.48, d (17.4) |
| 1' | 4.34, d (7.7) | 4.64, d (7.8) | 4.45, d (6.6) | 4.45, d (6.6) |
| 2' | 2.97, dd (9.3, 7.7) | 3.02, dd (7.8, 3.0) | 3.79, dd (6.6, 5.6) | 3.79, dd (6.6, 5.6) |
| 3' | 3.42, dd (9.3, 8.6) | 4.18, br t (3.0) | 4.12, m | 4.12, m |
| 4'a/b | 3.26, dd (9.3, 8.6) | 3.23, ddd (9.6, 9.2, 3.0) | 2.11, m/ 1.71, m | 2.11, m/ 1.71, m |
| 5' | 3.30, dq (9.3, 6.2) | 3.61, dq (9.6, 6.4) | 3.79, m | 3.79, m |
| 6' | 1.31, d (6.2) | 1.25, d (6.4) | 1.21, d (6.0) | 1.21, d (6.0) |
| 7'a/b | 3.62, s | 3.54, s | 5.20, s/ 4.87, s | 5.20, s/ 4.87, s |
| OH-3'[b] |  | 2.90, s |  |  |
| OH-4'[b] |  | 2.62, br d (9.2) |  |  |
| OH-5[b] |  |  | 4.24, s | 4.24, s |
| OH-14[b] |  |  | 4.69, br s | 4.69, br s |

[a]¹H NMR data (δ) were measured in CDCl₃ at 400 MHz for 6-9.
[b]D₂O exchangeable

TABLE 8

¹³C NMR data of compounds 8~13[a]

| position | 8 | 9 | 10 | 11 | 12 | 13 |
|---|---|---|---|---|---|---|
| 1 | 17.8 | 17.8 | 21.8 | 21.8 | 28.6 | 28.6 |
| 2 | 25.4 | 25.4 | 25.6 | 25.6 | 26.1 | 26.1 |
| 3 | 72.9 | 72.9 | 73.4 | 73.4 | 73.3 | 73.3 |
| 4 | 34.5 | 34.5 | 33.9 | 33.9 | 34.3 | 34.3 |
| 5 | 73.1 | 73.1 | 74.6 | 74.6 | 73.6[b] | 73.6[b] |
| 6 | 36.2 | 36.2 | 36.2 | 36.2 | 34.7 | 34.7 |
| 7 | 24.5 | 24.5 | 24.3 | 24.3 | 23.8 | 23.8 |
| 8 | 43.7 | 43.8 | 42.1 | 42.1 | 42.0 | 42.1 |
| 9 | 39.5 | 39.4 | 39.62 | 39.57 | 39.69 | 39.66 |
| 10 | 54.6 | 54.6 | 53.3 | 53.3 | 73.9[b] | 73.9[b] |
| 11 | 24.5 | 24.5 | 23.6 | 23.6 | 23.5 | 23.5 |
| 12 | 36.3 | 36.4 | 36.5 | 36.7 | 36.6 | 36.7 |
| 13 | 58.7 | 58.8 | 59.0 | 58.8 | 58.8 | 58.9 |
| 14 | 83.6 | 83.6 | 83.8 | 83.8 | 83.7 | 83.7 |
| 15 | 34.3 | 34.2 | 35.0 | 34.8 | 35.0 | 34.8 |
| 16 | 25.3 | 23.7 | 25.2 | 23.6 | 25.4 | 23.5 |
| 17 | 54.9 | 57.0 | 54.9 | 57.0 | 55.1 | 57.2 |
| 18 | 71.3 | 71.5 | 71.5 | 71.7 | 71.6 | 71.8 |
| 19 | 207.9 | 207.9 | 176.0 | 176.0 |  |  |
| 20 | 88.5 | 86.9 | 88.6 | 87.0 | 88.5 | 86.9 |
| 21 | 75.7 | 74.1 | 76.0 | 74.3 | 75.9 | 74.3 |
| 22 | 37.1 | 40.7 | 37.2 | 41.0 | 37.2 | 40.9 |
| 23 | 174.9 | 174.8 | 175.1 | 174.9 | 174.8 | 174.8 |
| 1' | 99.1 | 99.1 | 99.7 | 99.7 | 99.1 | 99.1 |
| 2' | 73.7 | 73.7 | 73.6 | 73.6 | 73.8 | 73.8 |
| 3' | 74.4 | 74.4 | 74.6 | 74.6 | 74.6 | 74.6 |
| 4' | 34.3 | 34.3 | 34.2 | 34.2 | 34.3 | 34.3 |
| 5' | 67.0 | 67.0 | 67.3 | 67.3 | 67.1 | 67.1 |
| 6' | 20.8 | 20.8 | 20.8 | 20.8 | 20.9 | 20.9 |
| 7' | 95.4 | 95.4 | 95.5 | 95.5 | 95.5 | 95.5 |

[a]¹³C NMR data (δ) were measured in CDCl₃ at 100 MHz for 8-11, at 150 MHz for 12 and 13.
[b]Interchangeable within the same column.

TABLE 9

¹H NMR Data of compounds 10-13[a]

| position | 10 | 11 | 12 | 13 |
|---|---|---|---|---|
| 1a/b | 2.28, m/1.82, m | 2.28, m/1.82, m | 1.93, m/1.47, m | 1.93, m/1.47, m |
| 2a/b | 1.92, m/1.51, m | 1.92, m/1.51, m | 1.87, m/1.76, m | 1.87, m/1.76, m |
| 3 | 4.22, br s | 4.22, br s | 4.15, br s | 4.15, br s |
| 4a/b | 2.08, m/1.74, m | 2.08, m/1.74, m | 1.84, m/1.43, m | 1.84, m/1.43, m |
| 6a/b | 1.89, m/1.62, m | 1.89, m/1.62, m | 1.90, m/1.43, m | 1.90, m/1.43, m |
| 7a/b | 2.05, m/1.16, m | 2.05, m/1.16, m | 2.00, m/1.06, m | 2.00, m/1.06, m |
| 8 | 2.01, m | 2.01, m | 1.90, m | 1.90, m |
| 9 | 1.43, m | 1.43, m | 1.31, m | 1.31, m |
| 11a/b | 1.89, m/1.59, m | 1.89, m/1.59, m | 1.93, m/1.68, m | 1.93, m/1.68, m |
| 12a/b | 1.74, m/1.43, m | 1.74, m/1.43, m | 1.81, m/1.53, m | 1.81, m/1.53, m |
| 15a/b | 1.80, m/1.71, m | 1.80, m/1.71, m | 1.84, m/1.76, m | 1.84, m/1.76, m |
| 16a/b | 1.89, m/1.67, m | 1.77, m/1.64, m | 1.87, m/1.76, m | 1.90, m/1.67, m |
| 17 | 2.08, m | 2.28, m | 2.15, m | 2.31, m |
| 18a/b | 4.26, d (10.4)/ 3.51, d (10.4) | 4.26, d (10.4)/ 3.47, d (10.4) | 4.23, d (10.2)/ 3.48, d (10.2) | 4.24, d (10.0)/ 3.44, d (10.0) |
| 21a/b | 4.33, d (10)/ 3.98, d (10) | 4.36, s | 4.33, dd (10.2, 0.8)/ 3.99, d (10.2) | 4.37, s |
| 22a/b | 2.65, d (17.6)/ 2.60, d (17.6) | 2.74, d (17.2)/ 2.44, d (17.2) | 2.66, d (17.8)/ 2.60, d (17.8) | 2.74, d (17.2)/ 2.45, d (17.2) |
| 1' | 4.44, d (6.9) | 4.44, d (6.9) | 4.47, d (6.7) | 4.47, d (6.7) |
| 2' | 3.81, dd (6.9, 5.3) | 3.81, dd (6.9, 5.3) | 3.81, dd (6.7, 5.3) | 3.81, dd (6.7, 5.3) |
| 3' | 4.15, ddd (5.3, 3.6, 1.6) | 4.15, ddd (5.3, 3.6, 1.6) | 4.15, ddd (5.3, 3.6, 2.0) | 4.15, ddd (5.3, 3.6, 2.0) |
| 4'a/b | 2.10, m/1.74, m | 2.10, m/1.74, m | 2.14, m/1.76, m | 2.14, m/1.76, m |
| 5' | 3.80, m | 3.80, m | 3.81, m | 3.81, m |
| 6' | 1.23, d (6.4) | 1.23, d (6.4) | 1.23, d (6.4) | 1.23, d (6.4) |
| 7'a/b | 5.23, s/4.91, s | 5.23, s/4.91, s | 5.24, s/4.91, s | 5.24, s/4.91, s |

[a]¹H NMR data (δ) were measured in CDCl₃ at 400 MHz for 10 and 11, at 600 MHz for 12 and 13.

There are more Embodiments provided as follows:

Embodiment 1

A pharmaceutical composition, includes:
an effective amount of a pharmaceutical compound being represented by formula (1):

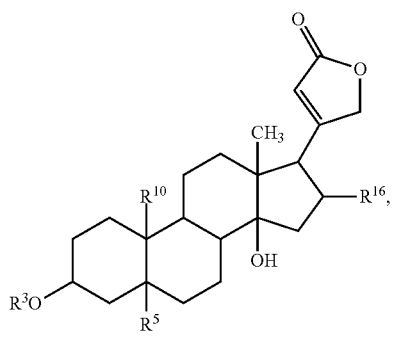

(1)

wherein the $R^3$ group is one of a hydrogen radical and a glycosyl group, the $R^5$ group is one of a hydrogen radical and a hydroxyl group, the $R^{10}$ group is one selected from a group consisting of a hydrogen radical, a hydroxyl group, a methyl radical, a formaldehyde group and a formic acid radical, and the $R^{16}$ group is one of a hydrogen radical and an acetic acid radical.

Embodiment 2

A pharmaceutical composition according to Embodiment 1 includes an effective amount of at least one being selected from a group consisting of a reevesioside A, a reevesioside B, a reevesioside C, a reevesioside D, a reevesioside E, a reevesioside F, and an epi-reevesioside F.

Embodiment 3

A pharmaceutical composition includes:
an effective amount of a pharmaceutical compound being represented by formula (2):

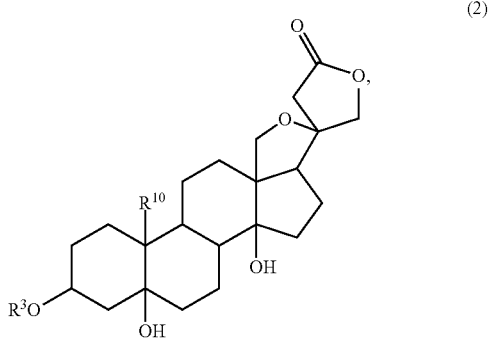

(2)

wherein the $R^3$ group is one of a hydrogen radical and a glycosyl group, the $R^{10}$ group is one selected from a group consisting of a hydrogen radical, a hydroxyl group, a methyl radical, a formaldehyde group, and a formic acid radical.

Embodiment 4

A pharmaceutical composition according to Embodiment 3 includes an effective amount of at least one being selected from a group consisting of a reevesioside G, a epi-reevesioside G, a reevesioside H, a epi-reevesioside H, a reevesioside I and a epi-reevesioside I.

Embodiment 5

A pharmaceutical composition according to above Embodiment includes a pharmaceutically acceptable carrier which is an excipient being one selected from a group consisting of a solvent, a dispersant, a coating, an antibacterial agent, an antifungal agent, a preservative absorbent, a delaying absorbent and a combination thereof.

Embodiment 6

A pharmaceutical composition according to above Embodiment is administered through one being selected from a group consisting of a vein, an oral, an inspiration, a nasal cavity, a rectum, a vagina, a hypoglossis and a combination thereof.

Embodiment 7

A pharmaceutical composition according to above Embodiment is processed into one being selected from a group consisting of a powder, a capsule, a tablet, a pill and a combination thereof.

Embodiment 8

A pharmaceutical composition according to above Embodiment is extracted from a *Reevesia formosana*.

Embodiment 9

A pharmaceutical composition according to above Embodiment is used for treating a cancer.

Embodiment 10

A pharmaceutical composition according to above Embodiment has a cytotoxic effect on cancer cells.

Embodiment 11

A cardenolide derivative, comprising a structure of formula 1

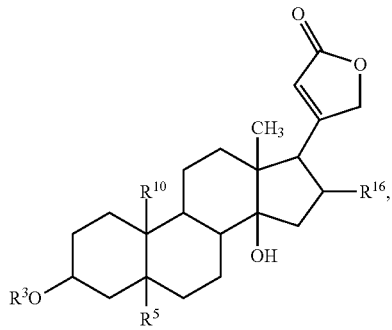

(1)

wherein the $R^3$ group is one of a hydrogen radical and a glycosyl group, the $R^5$ group is one of a hydrogen radical and a hydroxyl group, the $R^{10}$ group is one selected from a group consisting of a hydrogen radical, a hydroxyl group, a methyl radical, a formaldehyde group and a formic acid radical, and the $R^{16}$ group is one of a hydrogen radical and an acetic acid radical.

Embodiment 12

The cardenolide derivatives according to Embodiment 11 being selected from a group consisting of a reevesioside A, a reevesioside B, a reevesioside C, a reevesioside D, a reevesioside E, a reevesioside F and a epi-reevesioside F.

Embodiment 13

A cardenolide derivative, comprising a structure of formula 2:

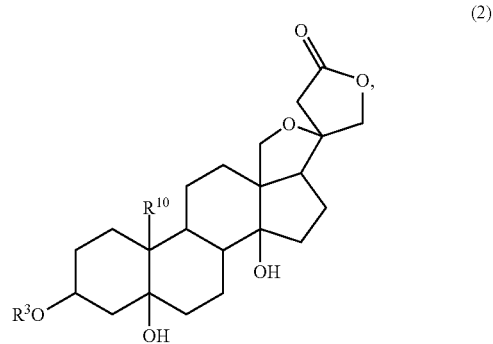

(2)

wherein the $R^3$ group is one of a hydrogen radical and a glycosyl group, the $R^{10}$ group is one selected from a group consisting of a hydrogen radical, a hydroxyl group, a methyl radical, a formaldehyde group, and a formic acid radical.

Embodiment 14

The cardenolide derivatives according to Embodiment 13 being extracted from a *Reevesia formosana*.

Embodiment 15

The cardenolide derivatives according to Embodiment 13 further comprising an effective amount of at least one being selected from a group consisting of a reevesioside G, an epi-reevesioside G, a reevesioside H, an epi-reevesioside H, a reevesioside I and an epi-reevesioside I.

Embodiment 16

The cardenolide derivatives as claimed in claim 15 used for treating a cancer.

What is claimed is:
1. A pharmaceutical composition, comprising:
an effective amount of a pharmaceutical compound being represented by formula 2:

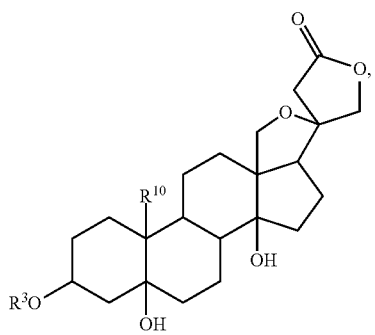

(2)

wherein the $R^3$ group is one of a hydrogen radical and a glycosyl group, the $R^{10}$ group is one selected from a group consisting of a hydrogen radical, a hydroxyl group, a methyl radical, a formaldehyde group, and a formic acid radical.

2. The pharmaceutical composition as claimed in claim 1 further comprising an effective amount of at least one being selected from a group consisting of a reevesioside G, an epi-reevesioside G, a reevesioside H, an epi-reevesioside H, a reevesioside I and an epi-reevesioside I.

3. The pharmaceutical composition as claimed in claim 1, wherein the pharmaceutically acceptable carrier is an excipient being one selected from a group consisting of a solvent, a dispersant, a coating, an antibacterial agent, an antifungal agent, a preservative absorbent, a delaying absorbent and a combination thereof.

4. The pharmaceutical composition as claimed in claim 1 being extracted from a *Reevesia formosana*.

5. The pharmaceutical composition as claimed in claim 1 used for treating a cancer.

6. The pharmaceutical composition as claimed in claim 1 having a cytotoxic effect on cancer cells.

7. A purified cardenolide derivative, comprising a structure of formula 2:

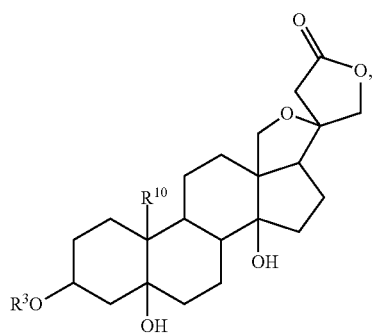

(2)

wherein the $R^3$ group is one of a hydrogen radical and a glycosyl group, the $R^{10}$ group is one selected from a group consisting of a hydrogen radical, a hydroxyl group, a methyl radical, a formaldehyde group, and a formic acid radical.

8. The purified cardenolide derivatives as claimed in claim 7 further comprising an effective amount of at least one being selected from a group consisting of a reevesioside G, an epi-reevesioside G, a reevesioside H, an epi-reevesioside H, a reevesioside I and an epi-reevesioside I.

9. The purified cardenolide derivatives as claimed in claim 7 being extracted from a *Reevesia formosana*.

10. The purified cardenolide derivatives as claimed in claim 7 used for treating a cancer.

* * * * *